United States Patent
Tang et al.

(10) Patent No.: US 10,287,236 B2
(45) Date of Patent: May 14, 2019

(54) PREPARATION OF THERMOPLASTIC EPOXIDIZED POLYMERS AND THERMOSETTING MATERIALS FROM TRIGLYCERIDES

(71) Applicant: University of South Carolina, Columbia, SC (US)

(72) Inventors: Chuanbing Tang, Columbia, SC (US); Zhongkai Wang, Columbia, SC (US); Liang Yuan, Columbia, SC (US)

(73) Assignee: University of South Carolina, Columbia, SC (US)

( * ) Notice: Subject to any disclaimer, the term of this patent is extended or adjusted under 35 U.S.C. 154(b) by 32 days.

(21) Appl. No.: 15/488,798

(22) Filed: Apr. 17, 2017

(65) Prior Publication Data
US 2017/0298007 A1   Oct. 19, 2017

Related U.S. Application Data

(60) Provisional application No. 62/324,026, filed on Apr. 18, 2016.

(51) Int. Cl.
*C07C 231/02* (2006.01)
*C08G 59/42* (2006.01)
(Continued)

(52) U.S. Cl.
CPC .......... *C07C 231/02* (2013.01); *C07D 301/14* (2013.01); *C07D 301/30* (2013.01); *C08F 120/36* (2013.01); *C08G 59/245* (2013.01); *C08G 59/4238* (2013.01); *C08G 59/686* (2013.01); *C08G 61/08* (2013.01); *C08G 2261/11* (2013.01); *C08G 2261/149* (2013.01); *C08G 2261/1412* (2013.01);
(Continued)

(58) Field of Classification Search
CPC .............. C07C 231/02; C08G 59/4238; C08G 59/686; C08G 59/245; C08G 61/08; C08G 2261/76; C08G 2261/418; C08G 2261/3324; C08G 2261/11; C08G 2261/149; C08G 2261/1432; C08G 2261/1426; C08G 2261/1412; C08G 2261/228; C07D 301/14; C07D 301/30; C08F 120/36
USPC ....................................................... 525/524
See application file for complete search history.

(56) References Cited

U.S. PATENT DOCUMENTS

2011/0060076 A1* 3/2011 Hefner, Jr. ............. C08G 59/28
523/400

OTHER PUBLICATIONS

Acar et al., "Novel Water Soluble Sonya Oil Polymer from Oxidized Soya Oil Polymer and Diethanol Amine", Journal of Macromolecular Science Part A, 50, 2013, pp. 287-296.
(Continued)

*Primary Examiner* — David T Karst
(74) *Attorney, Agent, or Firm* — Dority & Manning, P.A.

(57) ABSTRACT

A method i for forming an epoxidized polymer is provided. The method may include mixing an epoxidized plant oil with a synthetic epoxy resin and crosslinking the epoxidized plant oil and the synthetic epoxy resin using a curing agent. The epoxidized plant oil may be formed via: converting plant oil triglycerides to fatty amide alcohols via aminolysis using primary or secondary amines, converting the fatty amide alcohols to epoxidized fatty amide alcohols, and reacting the epoxidized fatty amide alcohols with vinyl monomers to obtain epoxidized plant oil monomers.

12 Claims, 11 Drawing Sheets

(51) Int. Cl.

| | |
|---|---|
| C08G 59/68 | (2006.01) |
| C08G 59/24 | (2006.01) |
| C07D 301/14 | (2006.01) |
| C07D 301/30 | (2006.01) |
| C08F 120/36 | (2006.01) |
| C08G 61/08 | (2006.01) |
| C07C 233/20 | (2006.01) |

(52) U.S. Cl.
CPC ............ C08G 2261/1426 (2013.01); C08G 2261/1432 (2013.01); C08G 2261/228 (2013.01); C08G 2261/3324 (2013.01); C08G 2261/418 (2013.01); C08G 2261/76 (2013.01)

(56) References Cited

OTHER PUBLICATIONS

Adekunle et al., "Biobased Composites Prepared by Compression Molding with a Novel Thermoset Resin from Soybean Oil and a Natural-Fiber Reinforcement", Journal of Applied Polymer Science, 116, : 2010, pp. 1759-1765.

Corma et al., "Chemical Routes for the Transformation of Biomass into Chemicals", Chemical Reviews, 107, 2007, pp. 2411-2502.

Edgar et al., "Advances in Cellulose Ester Performance and Application", Progress in Polymer Science, 26, 2001, pp. 1605-1688.

Fu et al., "Thermal and Mechanical Properties of Acrylated Expoxidized-Soybean Oil-Based Thermosets", Journal of Applied Polymer Science, 117, 2010, pp. 2220-2225.

Guner et al., "Polymers from Triglyceride Oils", Progress in Polymer Science, 31, 2006, pp. 631-670.

Lee et al., "Bio-Based Macroporous Polymer Nanocomposites Made by Mechanical Frothing of Acrylated Epoxidised Soybean Oil", Green Chemistry, 13, 2011, pp. 3117-3123.

Li et al., "New Soybean Oil-Styrene-Divinylbenzene Thermosetting Copolymers I Synthesis and Characterization", Journal of appied Polymer Science 80, 2001 pp. 658-670.

Li et al., "New Soybean Oil-Syrene-Divinylbenzene Thermosetting Copolymers-IV Good Damping Properties", Polymers for Advanced Technologies, 13, 2002, pp. 436-449.

Liu et al., "Thermal Processing of Starch-Based Polymers", Progress in Polymer Science, 34, 2009, pp. 1348-1368.

Lu et al., "New Sheet Molding Compound Resins from Soybean Oil I Synthesis and Characterization", Polymer, 46, 2005, pp. 71-80.

Meier et al., "Plant Oil Renewable Resources as Green Alternatives in Polymer Science", Chemical Society Reviews, 36, 2007, pp. 1788-1802.

Moon et al., "Cellulose Nanomaterials Review: Structure, Properties and Nanocomposites", Chemical Society Review, 40, 2011, pp. 3941-3994.

Pan et al., "High Biobased Content Epoxy-Anhydride Thermosets From Epoxidized Sucrose Esters of Fatty Acids", Biomacromolecules, 12, 2011, pp. 2416-2428.

Ratna et al., "Mechanical Properties and Morphology of Epoxidized Soybean-Oil-Modified Epoxy Resin", Polymer International, 50, 2001, pp. 179-184.

Sharma et al., "Addition Polymers from Natural Oils—A Review", Progress in Polymer Science, 31, 2006, pp. 983-1008.

Wilbon et al., "Progress in Renewable Polymers from Natural Terpenes, Terpenoids, and Rosin", Macromolecular rapid Communications, 34, 2013, pp. 8-37.

Williams et al., "Polymers from Renewable Resources: A Perspective for a Special Issue of Polymer Reviews", Polymer Reviews, 48, 2008, pp. 1-10.

Yao et al., "Controlled Polymerization of Next-Generation Renewable Monomers and Beyond", Macromolecules, 46, 2013, pp. 1689-1712.

* cited by examiner

PREPARATION OF THERMOPLASTIC EPOXIDIZED POLYMERS AND THERMOSETTING MATERIALS FROM TRIGLYCERIDES

PRIORITY INFORMATION

The present application claims priority to U.S. Provisional Patent Application Ser. No. 62/324,026 titled "Preparation of Thermoplastic Epoxidized Polymers and Thermosetting Materials from Triglycerides" of Tang, et al. filed on Apr. 18, 2016, the disclosure of which is incorporated by reference herein.

BACKGROUND

There is a growing concern about carbon source after the depletion of fossil fuels in the world of polymeric materials, as the majority of the commercialized polymer products are related to petrochemical resources, such as polystyrene, polyvinyl chloride, polypropylene, and polyethylene terephthalate. Renewable resources, such as carbohydrate, lignin, cellulose and plant oils, gain attention for the production of polymeric materials, due to their short term of reproducibility from biomass. Plant oils, mainly constituting of triglycerides, are extracted primarily from the seeds of oilseed plants. Besides the basic consumption as food, other applications are developed from this bio-renewable resource, like lubricants, biofuels, plasticizers, and construction materials. These triglycerides are also candidates as the building block of polymeric materials considering their natural abundance and inherent functionality, like the unsaturated double bond and ester groups. Challenges still present, including their heterogeneous and non-uniform structures.

Various kinds of biomass have been applied to prepare polymeric materials, such as cellulose, hemicellulose, lignin, starch, chitin, rosin acid, lactic acid, and plant oils. Among them, plant oils are one of the most abundant raw materials, which can be obtained primarily from plant seeds. Due to the unsaturation of fatty acid chains, plant oils have been widely used in the preparation of thermoset polymeric materials. Cationic polymerization of conjugate low saturation plant oils or copolymerization with divinylbenzene leads to thermosetting polymers. However, the reactivity of the unsaturated fatty acid double bonds is not high enough to obtain strong thermosetting polymers.

Another important method is to transfer the double bonds of plant oils to epoxy groups. The epoxy group can be further modified to obtain high reactive multi-functional monomers, such as acrylate plant oils. These acrylate plant oils can be used in the design of thermoset polymers. Epoxy resins are unique among all thermosetting resins with excellent resistance to chemicals and good thermal properties, which are widely used in coatings, adhesives, and matrices for composite materials. Epoxidized soybean oils are commercially available and have been used as plasticizers in plastic industry. However, the preparation and application of epoxy resins from plant oils is still limited, due to the poor mechanical properties of the epoxy resins derived from plant oils. There are two main reasons: the reactivity of the plant oil epoxy groups is too low; the number of epoxy groups in an epoxidized plant oil is too low.

SUMMARY

Objects and advantages of the invention will be set forth in part in the following description, or may be obvious from the description, or may be learned through practice of the invention.

A method is generally provided for forming an epoxidized polymer. In one embodiment, the method includes mixing an epoxidized plant oil with a synthetic epoxy resin and cross-linking the epoxidized plant oil and the synthetic epoxy resin using a curing agent. For example, the epoxidized plant oil may be formed via: converting plant oil triglycerides to fatty amide alcohols via aminolysis using primary or secondary amines, converting the fatty amide alcohols to epoxidized fatty amide alcohols, and reacting the epoxidized fatty amide alcohols with vinyl monomers to obtain epoxidized plant oil monomers.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "thermoplastic" is used herein to mean any material formed from a polymer which softens and flows when heated; such a polymer may be heated and softened a number of times without suffering any basic alteration in characteristics, provided heating is below the decomposition temperature of the polymer. Examples of thermoplastic polymers include, by way of illustration only, polyolefins, polyesters, polyamides, polyurethanes, acrylic ester polymers and copolymers, polyvinyl chloride, polyvinyl acetate, etc. and copolymers thereof.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally, methods of synthesizing epoxidized polymers from plant oils (e.g., plant triglycerides) are generally provided, along with their resulting polymeric materials and composites. For example, the preparation of epoxidized thermoplastic polymers from plant oils is generally provided, along with their curing to manufacture thermosetting materials and composites. These thermosetting polymers can be tailored to have varied mechanical properties, from soft elastomers to tough plastics. These polymers can also be used as shape memory materials. The epoxidized polymers described herein can be synthesized from all kind of plant oils, such as soybean oil, corn oil, etc., or mixtures thereof. In one embodiment, epoxidized polymers are prepared by polymerization of epoxidized monomers or by the epoxidization of polymers with unsaturated fatty acid side chains. These polymerization methods involve free radical polymerization, condensation polymerization, or ring-opening metathesis polymerization. These epoxidized polymers are then used together with reactive diluents, catalysts, crosslinkers, and toughing agents to give thermosetting polymers and composites. The thermosetting polymers and composites of the present disclosure can be used to replace epoxy resins made from petroleum chemicals.

There are two approaches to obtaining epoxidized polymers derived from plant oils. After polymerization, epoxidized polymers can be obtained. FIGS. 1A-1E show exemplary epoxidized fatty amides, monomers, and polymers from plant oils, amino alcohols that may be used for the preparation of epoxidized polymers.

In one embodiment, a method is provided where epoxidized plant oils are mixed with a synthetic epoxy resin, followed by crosslinking with some of the traditional curing agents. In this approach, triglycerides are converted to fatty amide alcohols via aminolysis using primary or secondary amines, followed by reacting with vinyl monomers to obtain monomers. After polymerization and epoxidization, the epoxidized polymers can be obtained. The polymerization includes radical polymerization, polycondensation, and ring-opening metathesis polymerization.

In another embodiment, the number of epoxy groups are increased in one molecule. Due to the higher number of epoxy groups, these epoxy resin show much better mechanical properties. In this approach, fatty amide alcohols are converted to epoxidized fatty amide alcohols. Epoxidized monomers are then obtained by reacting with vinyl monomers.

Figure 1A:
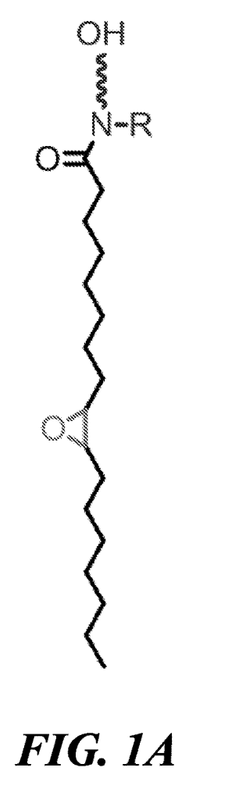
FIGS. 1A, 1B, 1C, 1D, and 1E show exemplary epoxidized fatty amides, monomers, and polymers from plant oils that are used, but not limited, for the preparation of epoxidized polymers.
Figure 1B:
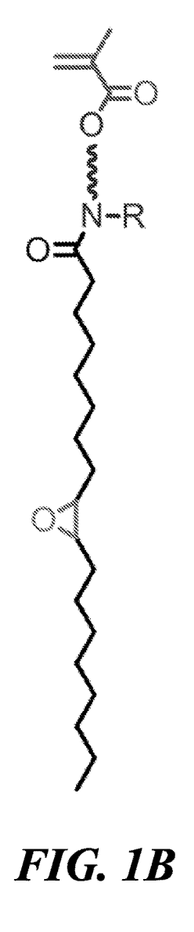
Figure 1C:
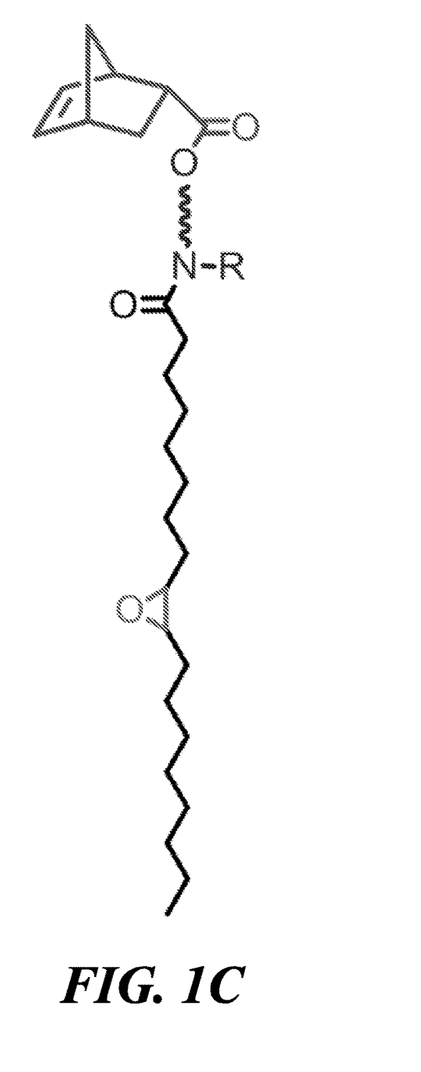
Figure 1D:
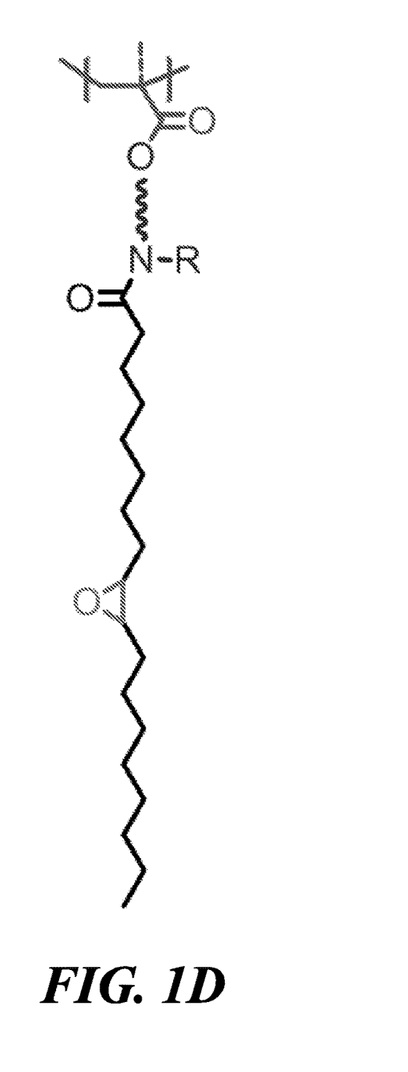
Figure 1E:
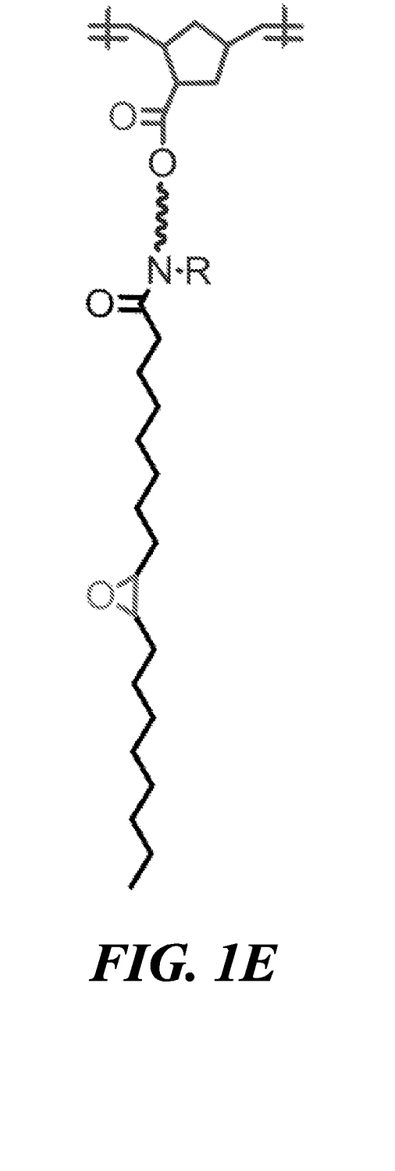
Figure 1F:
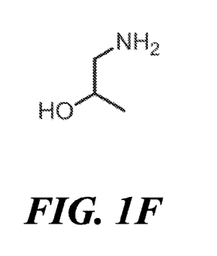
FIGS. 1F, 1G, 1H, 1I, 1J, 1K, 1L, 1M, 1N, 1O, 1P, 1Q, 1R, 1S, 1T, 1U, 1V, 1W, 1X, 1Y, and 1Z show exemplary monohydroxyl amines used for preparation of epoxidized monomers and polymers.
Figure 1G:
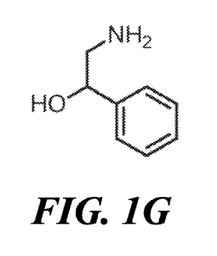
Figure 1H:
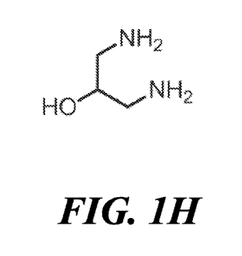
Figure 1I:
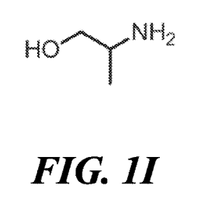
Figure 1J:
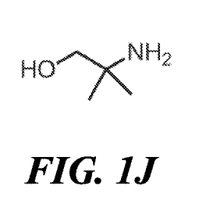
Figure 1K:
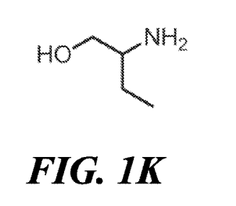
Figure 1L:
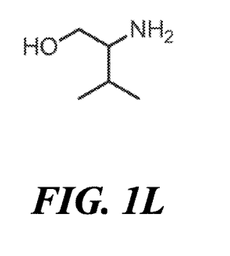
Figure 1M:
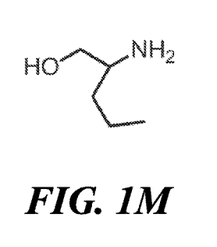
Figure 1N:
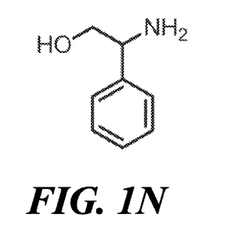
Figure 1O:
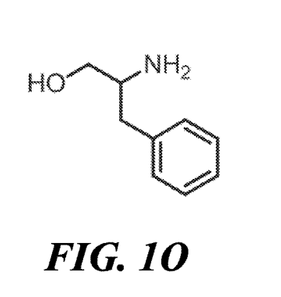
Figure 1P:
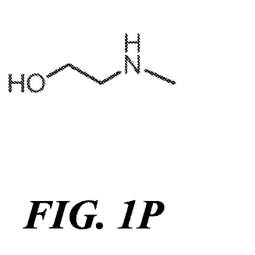
Figure 1Q:
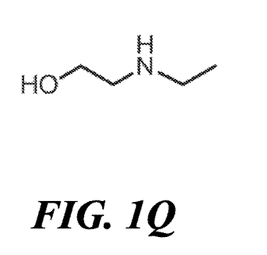
Figure 1R:
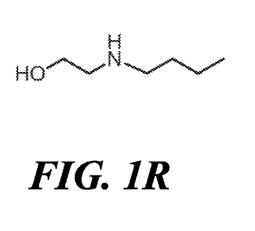
Figure 1S:
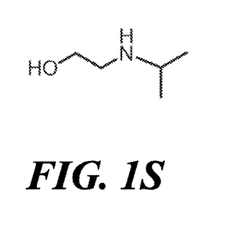
Figure 1T:
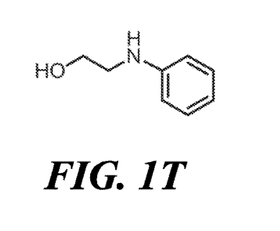
Figure 1U:
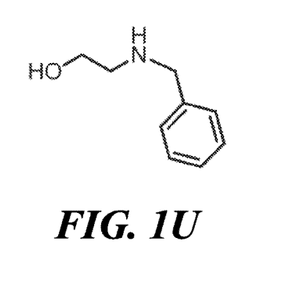
Figure 1V:
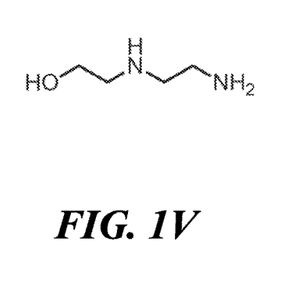
Figure 1W:
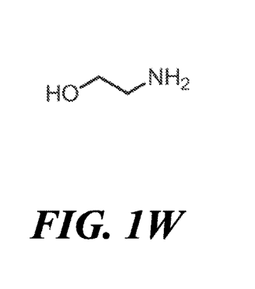
Figure 1X:
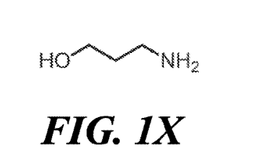
Figure 1Y:
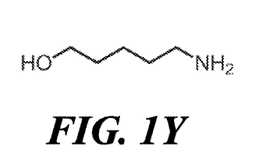
Figure 1Z:
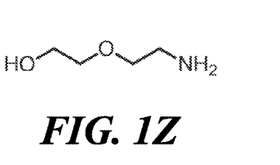

As illustrated in FIGS. 1F-1Z, various kinds of amino alcohols, but not limited, are used for the aminolysis of triglycerides and preparation of epoxidized polymers from plant oils.

Figure 2A:
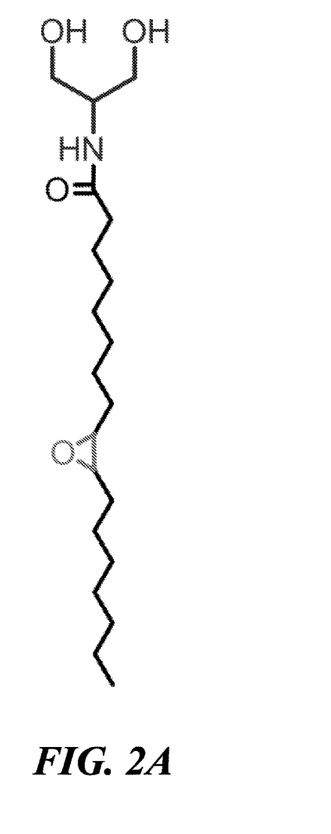
FIGS. 2A, 2B, 2C, and 2D show exemplary epoxidized dihydroxyl monomers particularly useful for forming polymers derived from plant oils such as polyesters and/or polyurethanes.
Figure 2B:
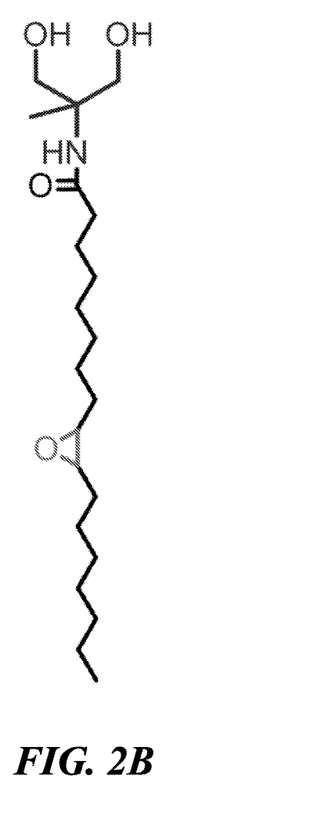
Figure 2C:
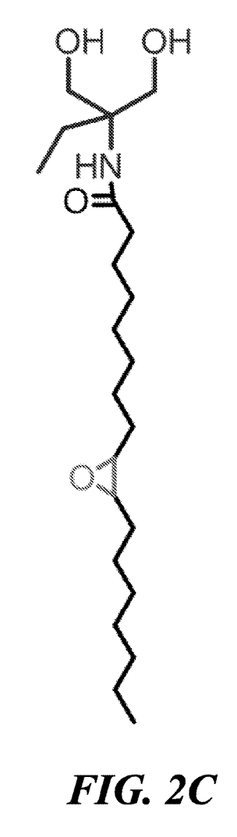
Figure 2D:
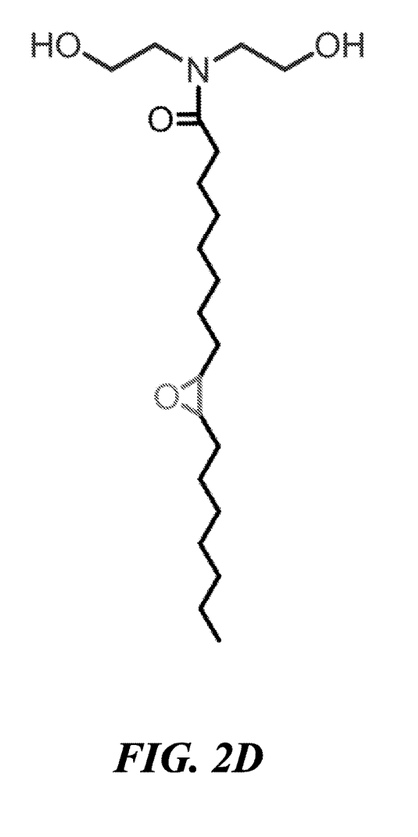
Figure 2E:
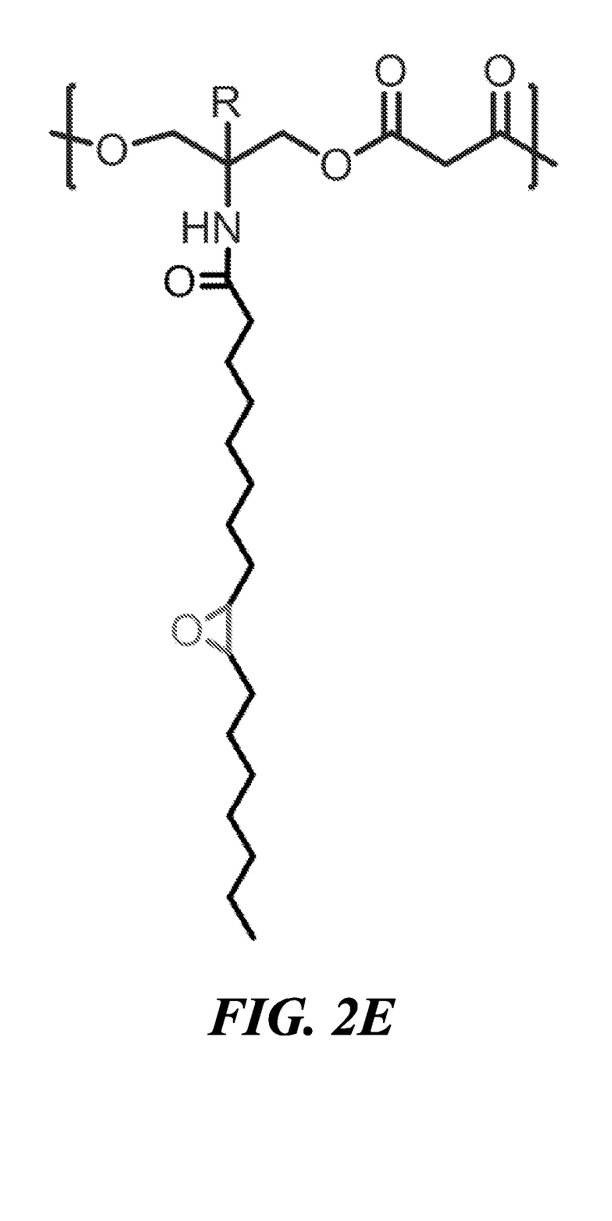
FIGS. 2E and 2F show exemplary epoxidized polyesters formed from polymerization of the exemplary epoxidized dihydroxyl monomers.
Figure 2F:
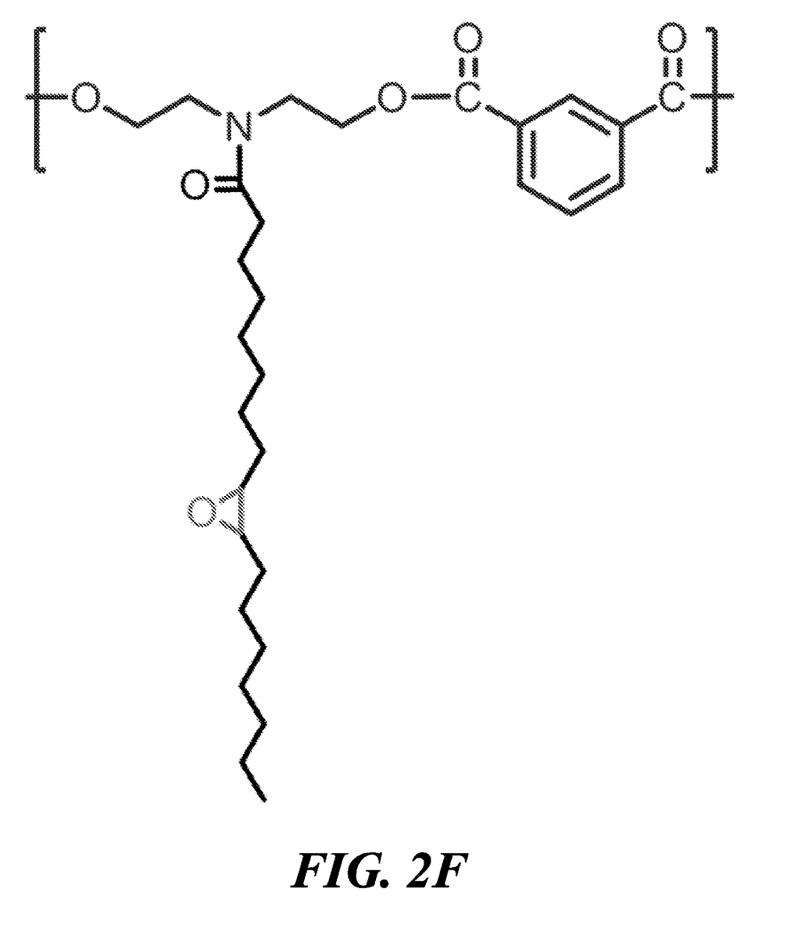
Figure 2G:
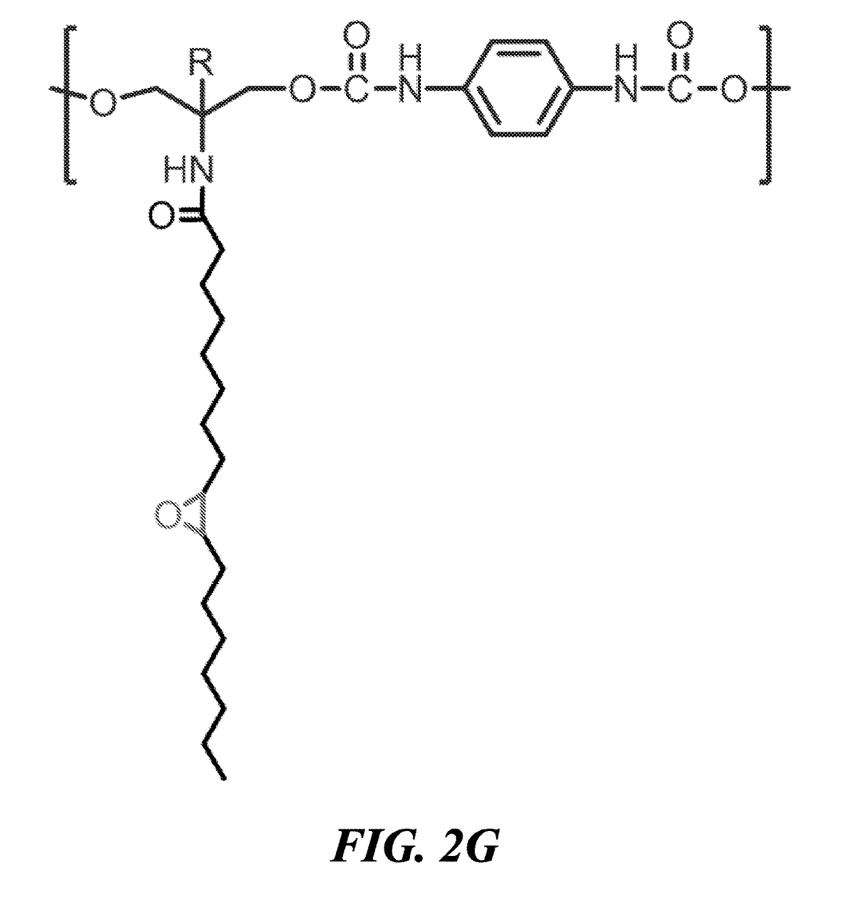
FIGS. 2G and 2H show exemplary epoxidized polyurethanes formed from polymerization of the exemplary epoxidized dihydroxyl monomers.
Figure 2H:
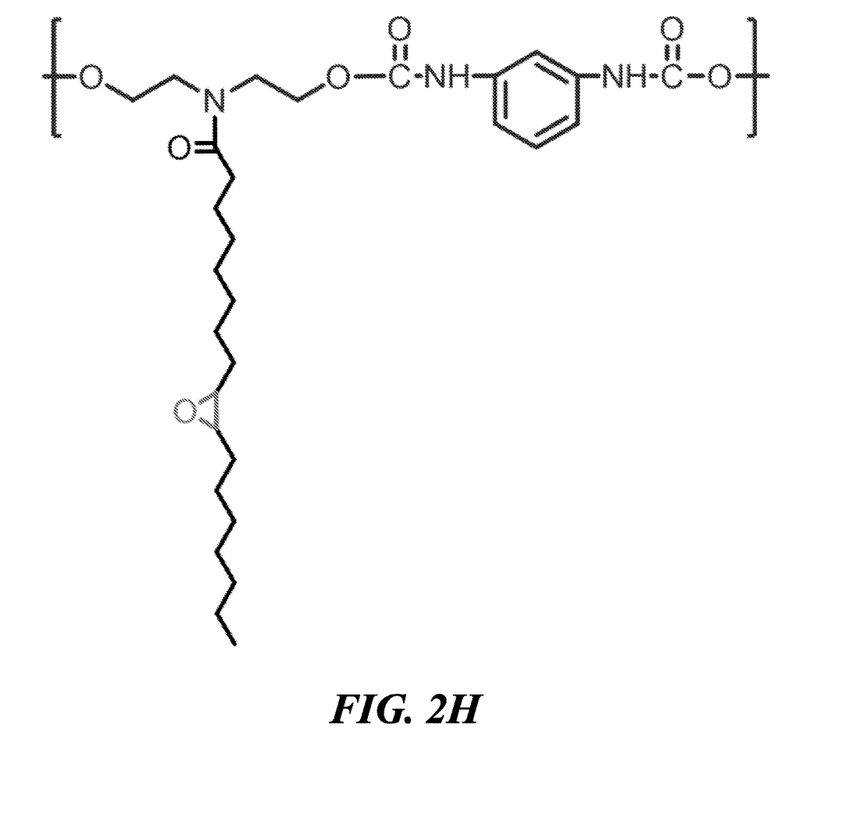

FIGS. 2A-2D shows some examples, but not limited, of the epoxidized dihydroxyl fatty amide from plant oils. Such dihydroxyl monomers, as shown in FIGS. 2A-2D, can be made into epoxidized polyesters (such as shown in FIGS. 2E and 2F) and polyurethanes (such as shown in FIGS. 2G and 2H. Moreover, (meth)acrylate monomers and epoxidized (meth)acrylate monomers (such as shown in FIGS. 1F-1Z) can also be polymerized via controlled radical polymerizations such as atom transfer radical polymerization (ATRP) and reversible addition fragmentation transfer polymerization (RAFT), which provides linear polymers with pendant fatty acid alkyl chains. Norbornene containing monomers can be polymerized through ring opening metathesis polymerization (ROMP).

These epoxidized polymers may then be used to prepare thermosetting polymers and composites by epoxy curing. These thermosetting polymers and composites show varied mechanical properties, from soft elastomers to hard and tough plastics.

In summary, the presently described methods provide an efficient approach to developing epoxidized thermoplastic polymers from plant triglycerides. Epoxidized polymers can be prepared via free radical polymerization, condensation polymerization, and ring-opening metathesis polymerization of plant triglycerides derived epoxidized monomers. The monomers involve epoxidized methyl methacrylate, acrylate, polyol, and norbornenes. Epoxidized polymers can also be prepared from polymers with unsaturated fatty acid side chains derived from plant triglycerides. The monomers involve epoxidized methyl methacrylate, acrylate, polyol, and norbornene. These polymers contain unsaturated fatty acid side chains, which can be converted to epoxy groups via epoxidation.

Additionally, methods are described to prepare thermosetting polymers using these epoxidized thermoplastic polymers. The epoxidized thermoplastic polymers, catalysts, crosslinking agents, and toughening agents were mixed, followed by thermal curing. The solvent can be organic solvents or reactive diluents. Traditional curing agents like amines, acids, or anhydrides are used.

Methods are also described to prepare thermosetting polymers by combining plant oil based epoxidized polymers with epoxy resin derived from fossil oil, such as diglycidyl ether of bisphenol-A. The introduction of commercial epoxy resin can further increase the mechanical properties of the products.

Methods are also described to prepare tough composites, which were prepared by embedding fibers or particles such as glass fibers, cellulose fibers, carbon black, and silica particles. These polymer matrix contain at least one epoxidized polymers derived from plant oils.

Thus, methods are described for the cross-linking of epoxidized polymers from plant oils to prepare thermosetting polymers. The epoxidized polymers from plant oils are cross-linked by reacting with difunctional or multifunctional curing agent including, but not limited to, amines, acids, alcohols, anhydrides. The amines that might be used, but not limited, are diethanolamine, propanediamine, methylene dicyclohexyl amine, poly(ethylene glyco) diamine, diaminobenzene, trimethyl hexamethylene diamine, etc. The acids that might be used, but not limited, are maleic acid, fumaric acid, succinic acid, glutaric acid, pimelic acid, suberic acid, adipic acid. The alcohols that might be used, but not limited, are ethylene glycol, 1,4-butanediol, 1,6-hexanediol, bisphenol A, sorbitol, diethanol amine. The anhydride that might be used, but not limited, are maleic anhydride, succinic anhydride, glutaric anhydride, phthalic anhydride, 4-methyl-1,2-cyclohexanedicarboxylic anhydride. Bases like, but not limited to, imidazoles, 4-dimethyl amino pyridine, 1,8-diazabicyclo[5.4.0]undec-7-ene, are used as catalyst. The curing temperature are in between 20 and 200° C.

As such, methods are described for the cross-linking of a mixture of epoxidized polymers from plant oils and epoxy resin from fossil oil to prepare thermosetting polymers. Epoxy resins involved are, but not limited, diglycidyl ether of bisphenol A, diglycidyl ether of bisphenol F. The mixture of epoxidized polymers from plant oils and epoxy resin from fossil oil are cross-linked by reacting with difunctional or multifunctional curing agents. The crosslinking methods used are the same as described previously.

Additionally, methods are described for thermosetting composites using at least one of the epoxidized polymers from plant oils as matrix. The introduction of fibers, particles to the polymer matrix provides the thermosetting composites with much higher tensile, bending, and impact strength. The fibers and particles used are, but not limited to, glass fibers, carbon fibers, cellulose fibers, silica particles, montmorillonite. The tough composites may find applications in aircraft, automotive, construction, and military industries.

The epoxy resins and their preparation methods described herein offer one or more of the following features: epoxidized fatty acid chains factionalized with mono-hydroxyl group, epoxidized vinyl monomers like, but not limited to, methacrylate, acrylate and norbornene monomers derived from plant oils, thermopalstic epoxidized polymers (e.g., polymethacrylate, polyacrylate, and polynorbornene derived from plant oils), epoxidized fatty acid chains factionalized with di-hydroxyl group, thermoplastic epoxidized polymers (e.g., polyesters and polyurethanes derived from plant oils), thermosetting polymers by epoxy curing of thermoplastic epoxidized polymers from plant oils, thermosetting polymers by epoxy curing of a mixture thermoplastic epoxidized polymers from plant oils and commercial epoxy resins, thermosetting composites with fibers or particles by epoxy curing of thermoplastic epoxidized polymers from plant oils, and/or thermosetting composites with fibers or particles by epoxy curing of a mixture of thermoplastic epoxidized polymers from plant oils and commercial epoxy resins.

EXAMPLES

Examples of epoxidized monomers, epoxidized polymers, thermosetting polymers, and composite materials derived from plant oils are described below.

Example 1

This example describes the synthesis of epoxidized fatty amides with mono-hydroxyl groups from plant oils. High oleic soybean oil and N-methyl amino ethanol were chosen as starting materials. The typical procedure was as follows: 106.7 g high oleic soybean oil was introduced to a 250 mL flask, and purged with N2 at 100° C. for 1 h. After cooling to 60° C., 47.6 mL of N-methyl amino ethanol and 1.6 mL of 30 wt % sodium methoxide in methanol was added. The reaction was allowed to react for 4 h and cooled to room temperature. Then 63 g meta-chloroperoxybenzoic acid (mCPBA) was added, the epoxidization of the double bonds on fatty amide alcohol was allowed to conduct for 4 h. After that, aqueous solution of sodium thiosulfate is added to the mixture to reduce the remaining mCPBA. Then, the mixture was washed with sodium bicarbonate solution and brine. The organic phase was dried with anhydrous MgSO4, then dried under vacuum to obtain epoxidized fatty amide alcohol.

Example 2

This example describes the synthesis of epoxidized methacrylate monomers from epoxidized fatty amide alcohol, although all epoxidized fatty amide alcohol containing mono-hydroxyl groups can be used. Epoxidized fatty amide alcohol from example 1 was chosen as an example, and methacrylate anhydride was chosen as reactant, but is not limited to such a reactant. The typical procedure was as follows: 116 g epoxidized fatty amide alcohol from example 1, 56 ml methacrylate anhydride, and 700 mg 4-dimethyl-aminopyridine (DMAP, as catalyst) were mixed in a 500 ml flask. The reaction was allowed to proceed at 60° C. for 12 h. Then, 100 ml THF and 20 ml water were added to quench the unreacted methacrylate anhydride. The mixture was washed with sodium bicarbonate solution and brine. The product was extracted by dimethyl chloride, the organic phase was dried with anhydrous MgSO4, then dried under vacuum to obtain epoxidized methacrylate monomers.

Example 3

This example describes synthesis of epoxidized acrylate monomers from epoxidized fatty amide alcohol. It is noted that all epoxidized fatty amide alcohol that contain mono-hydroxyl groups can be used. Here, epoxidized fatty amide alcohol from example 1 was chosen as an example, with acrylate chloride as reactant, but is not limited to such a reactant. The typical procedure was as follows: 100 g epoxidized fatty amide alcohol from example 1, 27 ml triethylamine, and 100 ml dimethyl chloride were mixed in a 500 ml flask. The flask was cool down by ice/water bath. Then, 33.8 ml acrylate chloride in 24 ml dimethyl chloride was added dropwise. The reaction was allowed to proceed at room temperature for 12 h. After that, the solid ammonium chloride salt was removed by filtration. The mixture was washed with sodium bicarbonate solution and brine. The product was extracted by dimethyl chloride, the organic phase was dried with anhydrous MgSO4, then dried under vacuum to obtain epoxidized acrylate monomers.

Example 4

This example describes synthesis of epoxidized norborene monomers from epoxidized fatty amide alcohol, although all epoxidized fatty amide alcohol containing mono-hydroxyl groups can be used. Epoxidized fatty amide alcohol from example 1 was chosen as an example, and exo-5-norbornenecarboxylic acid was chosen as a reactant, but is not limited to such a reactant. The typical procedure was as follows: 10 g epoxidized fatty amide alcohol from example 1, 6 g pivalic anhydride, 4.4 g exo-5-norbornenecarboxylic acid, 44 mg 4-dimethylaminopyridine (DMAP, as catalyst), and 30 ml THF were mixed in a 100 ml flask.

The reaction was allowed to proceed at 60° C. for 20 h. After that, the mixture was dilute with dimethyl chloride, washed with sodium bicarbonate solution and brine. The organic phase was dried with anhydrous MgSO4, then dried under vacuum to obtain epoxidized norborene monomers.

Example 5

This example describes free radical polymerization of epoxidized methacrylate monomers from epoxidized fatty amide alcohol, although all epoxidized methacrylate monomers can be used. The epoxidized methacrylate monomer from example 2 was chosen as an example. The typical procedure was as follows: 25 g epoxidized methacrylate monomer from example 2, 40 ml toluene, and 80 mg AIBN (as thermal initiator) were mixed in a 50 ml flask. The flask was purge with N2 for 15 min. The reaction was allowed to proceed at 80° C. for 12 h. After that, the solution was precipitated in methanol, then dried under vacuum to obtain epoxidized methacrylate polymers.

Example 6

This example describes free radical polymerization of epoxidized acrylate monomers from epoxidized fatty amide alcohol, although all epoxidized acrylate monomers can be used. Epoxidized methacrylate monomer from example 3 was chosen as an example. Typical procedure was as follows: 80 g epoxidized methacrylate monomer from example 2, 80 ml toluene, and 400 mg BPO (as thermal initiator) were mixed in a 250 ml flask. The flask was purge with N2 for 15 min. The reaction was allowed to proceed at 100° C. for 24 h. After that, the solution was precipitated in methanol, and then dried under vacuum to obtain epoxidized acrylate polymers.

Example 7

This example describes ring opening metathesis polymerization of epoxidized norborene monomers from epoxidized fatty amide alcohol, although all epoxidized norborne monomers can be used. Epoxidized norborne monomer from example 4 was chosen as an example. Typical procedure was as follows: 3 g epoxidized norborne monomer from example 4 was dissolved in 30 ml dry THF in a 50 ml flask. The flask was purge with N2 for 15 min. 25 mg Grubbs 3rd generation catalyst in 5 ml dry THF was purged with N2 for 15 min and transfer to the flask. The reaction was allowed to proceed at room temperature for 1 h. After that, ethyl vinyl ether was added to stop the polymerization. The solution was precipitated in methanol, and then dried under vacuum to obtain epoxidized norborene polymers.

Example 8

This example describes living/controlled radical polymerization of epoxidized methacrylate monomers, of which any epoxidized methacrylate monomers can be used. Atom transfer radical polymerization (ATRP) was used to polymerize epoxidized methacrylate monomer from example 2 as an example, although other monomers can be utilized. A typical procedure was as follows: 4 g epoxidized methacrylate monomer from example 2, 1 ml DMF, 19 mg ethyl bis(2-bromoisobutyrate), 23 mg tris(2-(dimethylamino) ethyl) amine (Me6TREN) and 14.4 mg CuBr were mixed in a 25 ml flask. The flask was purge with N2 for 15 min. The reaction was allowed to proceed at 90° C. for 12 h. After that, the solution was precipitated in methanol, and then dried under vacuum to obtain epoxidized methacrylate polymers.

Example 9

This example describes synthesis of epoxidized fatty amides with di-hydroxyl groups from plant oils. High oleic soybean oil and 2-aminopropane-1,2-diol were chosen as starting materials. Typical procedure was as follows: 106.7 g high oleic soybean oil was introduced to a 250 ml flask, purge with N2 at 100° C. for 1 h. After cool to 60° C., 35 g 2-aminopropane-1,2-diol and 1.6 ml 30 wt % sodium methoxide in methanol was added. The reaction was allowed to react for 4 h and cool to room temperature. Then, 63 g meta-chloroperoxybenzoic acid (mCPBA) was added, the epoxidization of the double bonds on fatty amide alcohol was allowed to conduct for 4 h. After that, aqueous solution of sodium thiosulfate is added to the mixture to reduce the remaining mCPBA. Then, the mixture was washed with sodium bicarbonate solution and brine. The organic phase was dried with anhydrous MgSO4, then dried under vacuum to obtain epoxidized fatty amides with di-hydroxyl groups.

Example 10

This example describes condensation polymerization of epoxidized fatty amides with di-hydroxyl groups, although all epoxidized monomers can be used. Epoxidized monomer from example 9 was chosen as an example, typical procedures are as follows: 3.5 g epoxidized monomer from example 9, 0.9 g oxalic acid, and PbO were added to a 10 ml flask. The reaction was allowed to proceed at 180° C. under vacuum for 8 h to obtain epoxidized polyester.

Example 11

The example shows preparation of epoxidization of plant oil based polymer from plant oils. The polymers derived from plant oils can be used in any of the methods described herein. Methacrylate polymers derived from soybean oil (PSBMA) were chosen as an example, with the typical procedure being: 3 g PSBMA was dissolved in 30 ml dimethyl chloride, then 2.8 g meta-chloroperoxybenzoic acid (mCPBA) was added. The reaction was allowed to conduct for 12 h, precipitated in cold methanol for 3 times, and then dried under vacuum to obtain epoxidized PSBMA.

Example 12

This example describes curing of epoxidized polymers from example 5-11. Here, the epoxidized methacrylate polymer from example 5 was chosen as an example. 4-methyl-1,2-cyclohexanedicarboxylic anhydride, but not limited, was used as cross-linker. Base like, but not limited to, 1,8-diazabicyclo[5.4.0]undec-7-ene was used as catalyst. Typical curing procedures are as follows: 1.2 g epoxidized methacrylate polymers from example 5, 252 mg 4-methyl-1,2-cyclohexanedicarboxylic anhydride, and 15 mg 1,8-diazabicyclo[5.4.0]undec-7-ene were dissolved in 5 ml THF. The mixture was then transfer to a Teflon mold. After dry, the curing reaction was conducted at 100° C. for 12 h to obtain thermosetting materials.

Example 13

This example describes curing of a mixture epoxidized polymers and commercial epoxy resin. The epoxidized methacrylate polymers from example 5 was chosen, with diglycidyl ether of bisphenol A, as an example. 4-methyl-1,2-cyclohexanedicarboxylic anhydride, but not limited, was used as crosslinker. Base like, but not limited to, 1,8-diazabicyclo[5.4.0]undec-7-ene was used as catalyst. Typical curing procedures are as follows: 0.6 g epoxidized methacrylate polymers from example 5, 0.6 g diglycidyl ether of bisphenol A, 252 mg 4-methyl-1,2-cyclohexanedicarboxylic anhydride, and 15 mg 1,8-diazabicyclo[5.4.0]undec-7-ene were dissolved in 5 ml THF. The mixture was then transfer to a Teflon mold. After dry, the curing reaction was conducted at 100° C. for 12 h to obtain thermosetting materials.

Example 14

This example describes preparation of composites using epoxidized polymers from plant oils as polymer matrix. Epoxidized methacrylate polymers from example 5 was chosen, along with glass fiber as an example. 4-methyl-1,2-cyclohexanedicarboxylic anhydride, but not limited, was used as crosslinker. Base like, but not limited to, 1,8-diazabicyclo[5.4.0]undec-7-ene was used as catalyst. Typical curing procedures are as follows: 1.2 g epoxidized methacrylate polymers from example 5, 252 mg 4-methyl-1,2-cyclohexanedicarboxylic anhydride, and 15 mg 1,8-diazabicyclo[5.4.0]undec-7-ene were dissolved in 5 ml THF. The mixture was then transfer to a Teflon mold containing glass fibers. After dry, the curing reaction was conducted at 100° C. for 12 h to obtain thermosetting materials.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming an epoxidized polymer, the method comprising: mixing an epoxidized plant oil with a synthetic epoxy resin; and
    crosslinking the epoxidized plant oil and the synthetic epoxy resin using a curing agent wherein, the epoxidized plant oil is formed via:
        converting plant oil triglycerides to fatty amide alcohols via aminolysis using primary or secondary amines; converting the fatty amide alcohols to epoxidized fatty amide alcohols; and
        reacting the epoxidized fatty amide alcohols with vinyl monomers to obtain epoxidized plant oil monomers.

2. The method of claim 1, wherein the plant oil triglycerides are converted to fatty amide alcohols via aminolysis using primary amines.

3. The method of claim 2, wherein the primary amines comprise at least one primary amine having a structure selected from the group consisting of:

4. The method of claim 1, wherein the plant oil triglycerides are converted to fatty amide alcohols via aminolysis using secondary amines.

5. The method of claim 4, wherein the secondary amines comprise at least one primary amine having a structure selected from the group consisting of:

6. The method of claim 1, wherein the vinyl monomers comprise methacrylate monomers, acrylate monomers, norbornene monomers, or mixtures thereof.

7. A method of forming an epoxidized polymer, the method comprising: mixing an epoxidized plant oil with a synthetic epoxy resin; and crosslinking the epoxidized plant oil and the synthetic epoxy resin using a curing agent, wherein the epoxidized plant oil is formed via:
    converting plant oil triglycerides to fatty amide alcohols via aminolysis using primary or secondary amines; and
    reacting the fatty amide alcohols with vinyl monomers to obtain epoxidized plant oil monomers.

8. The method of claim 7, wherein the plant oil triglycerides are converted to fatty amide alcohols via aminolysis using primary amines.

9. The method of claim 8, wherein the primary amines comprise at least one primary amine having a structure selected from the group consisting of:

-continued

10. The method of claim 7, wherein the plant oil triglycerides are converted to fatty amide alcohols via aminolysis using secondary amines.

11. The method of claim 10, wherein the secondary amines comprise at least one primary amine having a structure selected from the group consisting of:

12. The method of claim 7, wherein the vinyl monomers comprise methacrylate monomers, acrylate monomers, norbornene monomers, or mixtures thereof.

* * * * *